(12) United States Patent
Thompson et al.

(10) Patent No.: US 9,915,615 B2
(45) Date of Patent: Mar. 13, 2018

(54) DETECTION OF BACTERIA OR SOMATIC CELLS IN ORGANIC SAMPLES BY APT BASED LUMINESCENCE

(75) Inventors: Maurice William Thompson, Herefordshire (GB); Andrew Prail, Herefordshire (GB); David Kent Wright, Herefordshire (GB)

(73) Assignee: KRYSIUM TECHNOLOGIES LIMITED, Loeminster, Herefordshire (GB)

( * ) Notice: Subject to any disclaimer, the term of this patent is extended or adjusted under 35 U.S.C. 154(b) by 775 days.

(21) Appl. No.: 12/596,290

(22) PCT Filed: Apr. 14, 2008

(86) PCT No.: PCT/GB2008/001302
§ 371 (c)(1),
(2), (4) Date: Mar. 22, 2010

(87) PCT Pub. No.: WO2008/125840
PCT Pub. Date: Oct. 23, 2008

(65) Prior Publication Data
US 2010/0184124 A1    Jul. 22, 2010

(30) Foreign Application Priority Data

Apr. 17, 2007 (GB) .................................. 0707345.5

(51) Int. Cl.
*C12Q 1/04* (2006.01)
*G01N 21/76* (2006.01)
*G01N 33/04* (2006.01)

(52) U.S. Cl.
CPC ............... *G01N 21/76* (2013.01); *C12Q 1/04* (2013.01); *G01N 33/04* (2013.01)

(58) Field of Classification Search
CPC ................................... G01N 21/76; C12Q 1/04
See application file for complete search history.

(56) References Cited

U.S. PATENT DOCUMENTS 4,390,274 A * 6/1983 Berthold et al. ................. 356/36
6,660,469 B1 * 12/2003 Wright et al. ...................... 435/4

FOREIGN PATENT DOCUMENTS

| CN | 1876829 A | 3/2006 |
| GB | 2350421 A | 11/2000 |
| WO | 9109300 A1 | 6/1991 |

* cited by examiner

*Primary Examiner* — Vera Afremova
(74) *Attorney, Agent, or Firm* — Thedford I. Hitaffer; Hitaffer & Hitaffer, PLLC

(57) ABSTRACT

A method of testing an organic sample to provide an indication of the level of bacteria and/or number of somatic cells present in the sample, the method including collecting the sample and contacting the sample with a reagent which reacts with ATP to produce light emissions, and subsequently, at the beginning (O) of a measurement period (A, B), contacting the sample with an extractant in the presence of the reagent, the extractant rupturing cells present in the sample to release cell-bound ATP to react with the reagent to produce light emissions, and immediately after contacting the sample with the extractant, detecting the light emissions with a light detecting device (18), and the method includes during an initial measurement period (A) immediately after contacting the sample with the extractant, detecting the level of light emissions, and in a subsequent measurement period (B), detecting the level of light emissions, statistically analyzing the detected values to determine a rate of change of light emissions during the subsequent measurement period, due to cell-bound ATP being released and reacting with the reagent, and at least where the thus determined rate of change of light emissions indicates a level of bacteria and/or somatic cells in the sample above a threshold, generating a signal (33).

20 Claims, 1 Drawing Sheet

DETECTION OF BACTERIA OR SOMATIC CELLS IN ORGANIC SAMPLES BY APT BASED LUMINESCENCE

CROSS REFERENCE TO RELATED APPLICATIONS

This application is a continuation of International Application No. PCT/GB2008/001302, filed Apr. 14, 2008, which claims priority from GB Patent Application No. 0707345.5, filed Apr. 17, 2007. The disclosures of both applications are incorporated herein by reference.

This invention relates to a method of testing an organic sample, such as a biological fluid, and more particularly to provide an indication of the number of cells present in a sample.

In our previous patent U.S. Pat. No. 6,660,469 there is disclosed a method in which a biological fluid sample is collected on a dipstick which is impregnated with a reagent which reacts with adenosine triphosphate ("ATP") to produce light emissions. To perform testing to give an indication of the number of somatic or other cells present, the dipstick is placed in a testing container. The testing container is placed in a light detecting device, where the dipstick is plunged through a membrane in the testing container, to bring the sample and reagent into contact with an extractant. The extractant ruptures any cells present thereby releasing ATP from the cells. The ATP reacts with the reagent to produce light emissions which are detected by the light detecting device. The level of light emissions detected, gives an indication of the number of cells present from which the ATP is released.

This testing method is simple and can readily be performed in the field, i.e. by a dairyman in the normal course of milking. For example during milking, a plurality of samples may be taken each on dipsticks of individual testing containers, and the samples may be tested severally by placing each testing container in the light detecting device.

In the prior method, a false indication of the level of bacteria and/or number of somatic and other cells present in a sample can be given, for example, or other material which reacts with the reagent to produce light emissions (hereinafter collectively called "free ATP"), if the sample contains free ATP i.e. ATP which is not bound within the cells. Particularly where the biological fluid sample is milk, it is not uncommon for the milk to contain some free ATP. This free ATP could be present due to some condition of the animal from which the milk sample was obtained, or may be due to contamination e.g. introduced during taking of the sample.

Whereas the prior method was particularly but not exclusively developed for testing milk samples to determine if an animal giving the milk has mastitis or another infection, which will affect the number of somatic cells present in its milk, the presence of free ATP may by the prior method, lead to an indication that the animal has an infection when it does not, because the free ATP reacts with the reagent to produce light emissions as well as released cell-bound ATP. As explained above, the free ATP may be present in the sample for reasons other than the animal having mastitis, such as for example, contamination.

Thus whereas the previous method is reliable where the level of free ATP in the sample is low, it will be appreciated that it is advantageous to be able at least to exclude the effects of free ATP from the results of the testing method.

In other prior proposals, efforts have been made to exclude free ATP before cell-bound ATP is extracted. Such proposals have largely relied upon complex chemical techniques to destroy, neutralise or separate the free ATP in the sample prior to cells in the sample being ruptured to release cell-bound ATP, and such techniques cannot be readily performed otherwise than under laboratory conditions. Moreover, in such prior proposals, the sample needs to be isolated from the reagent until the cells are ruptured and cell-bound ATP is released, so that the reagent and free ATP do not come into contact.

Other proposals involve efforts to determine the level of free ATP in the sample, before the cells are ruptured to release cell-bound ATP. However, such prior proposed testing methods are again complex and have required multiple method steps and/or involved the use of complicated test equipment. Such prior proposals have maintained the sample out of contact with the reagent until testing is to be commenced, when the sample is contacted first with reagent, and light emissions are detected over an initial testing period before the cells are ruptured to release cell-bound ATP, to give a measure of the amount of free ATP present. After such an initial testing period, the sample, in the presence of the reagent, is then contacted with extractant, to extract the cell-bound ATP, and then during a subsequent testing period, light emissions are detected again.

In such prior methods because the determination of the level of free ATP is made in the initial testing period, before the cell-bound ATP is extracted, and the level of free ATP available to generate light emissions when reacting with the reagent in the subsequent testing period, will have reduced from the level determined during the initial testing period, using the determination of the level of free ATP in the initial testing period as an indicator of the level of free ATP in the sample, can give rise to false readings which may indicate that the level of cell-bound ATP is lower than it is.

Thus hithertofore, no simple testing method which can readily be performed outside of a laboratory has been available which is able reliably to account for free ATP which may be present in the sample being tested.

According to a first aspect of the present invention we provide a method of testing an organic sample to provide an indication of the level of bacteria and/or number of somatic cells present in the sample, the method including collecting the sample and contacting the sample with a reagent which reacts with ATP to produce light emissions, and subsequently, at the beginning of a measurement period, contacting the sample with an extractant in the presence of the reagent, the extractant rupturing cells present in the sample to release cell-bound ATP to react with the reagent to produce light emissions, and immediately after contacting the sample with the extractant, detecting the light emissions with a light detecting device, and the method includes during an initial measurement period immediately after contacting the sample with the extractant, detecting the level of light emissions, and in a subsequent measurement period, detecting the level of light emissions, statistically analysing the detected values to determine a rate of change of light emissions during the subsequent measurement period, due to cell-bound ATP being released and reacting with the reagent, and at least where the thus determined rate of change of light emissions indicates a level of bacteria and/or somatic cells in the sample above a threshold, generating a signal.

The method of the invention relies on the discovery that when the sample is contacted with the extractant, there is a time i.e. during the initial measurement period, as the cell-bound ATP begins to be released, when the contribution to light emissions due to the released cell-bound ATP reacting with the reagent, will be minimal, and thus determining the overall level of light emissions during the initial measurement period, allows the contribution to light emissions from other than the released ATP to be compensated for.

Thus the method of the invention enables a determination of the rate of change of released ATP to be made as part of a simple testing method which readily can be performed outside of laboratory conditions.

The organic sample may be fluid collected on a dipstick having an attachment part to which a predetermined volume of the sample may attach as the dipstick is dipped into the sample which is to be collected. The attachment part may be impregnated with the reagent so that there is no need for a person performing the method, to do anything other than collect the sample on the dipstick, in order to contact the sample with the reagent.

The sample may be contacted with the extractant at a later time, but preferably soon after e.g. within 30 minutes after collection on the dipstick, and preferably as soon as possible, e.g. within a few seconds. Thus in the event that a large amount of free ATP is present in the sample, by the time the sample is contacted with the extractant, the amount of reagent available for reacting with the released ATP will not have been significantly depleted.

The testing method relies upon the amount of the cell-bound ATP which is released upon contacting the sample with the extractant, building up from a nil level during the initial measurement period, and not the actual amount of free ATP in the sample. Thus the spending of some free ATP in the period from when the sample is collected to the beginning of the initial measurement period, is not significant to the testing method.

After collecting the sample on the dipstick, and preferably soon after collection of the sample, to minimise the risk of contamination, the dipstick may be placed in a container. The container may be a testing container which may contain the extractant, in which case the extractant is preferably maintained out of contact with the sample and enzyme on the dipstick, e.g. by the presence of a membrane in the testing container, until the beginning of the measurement period.

In another example, the container in which the dipstick is placed after collecting the sample, may be a storage container, and the dipstick may be transferred to a testing container which contains the extractant, immediately prior to the measurement period.

In each case, as suggested in our previous patent, the sample may be contacted with the extractant by moving the dipstick in the testing container so as either to rupture the membrane, where a membrane is provided, to separate the extractant from the remainder of the container, or simply to move the dipstick down into contact with the extractant, where no membrane is provided. This dipstick movement may be achieved with the testing container positioned in a chamber of a light detecting device, by moving a part of the light detecting device, such as a lid thereof, to engage an end of the dipstick remote from the attachment part, and to move the dipstick.

Thus by detecting all the light emissions during the subsequent measurement period, some of which will be due to the reaction of free ATP with the reagent and some of which will be due to the reaction of released cell-bound ATP with the reagent, the contribution to the light emissions by the released cell-bound ATP reacting with the reagent can be reasonably accurately determined.

The method may include, during the initial measurement period, where the level of light emissions detected exceeds a maximum, providing a warning. A very high level of light emissions detected in the initial measurement period could indicate that the sample is contaminated, or that, in the case of a milk test, that the animal from which the sample was taken, has a serious infection. Where the level of free ATP indicated by the very high level of light scintillations in the initial measurement period is so high that this would make statistical analysis of the detected values of light emissions detected throughout the measurement period to determine the level of released ATP, impossible, the test may be curtailed at that point. However even if a high level of free ATP is indicated by light scintillations in the initial measurement period, it may still be possible to continue with the remainder of the test.

BRIEF DESCRIPTION OF DRAWINGS

Embodiments of the invention will now be described with reference to the accompanying drawings in which:

Referring to FIG. 1 there is shown an apparatus 10 for performing a testing method on a milk sample collected from a cow during milking. The method and apparatus 10 may though be applied for testing biological fluids samples, in general, for animals, humans or otherwise, or indeed for testing any organic sample which may have cells, such as somatic or bacterial cells, of which it is desired to determine the level in the sample. A solid organic sample may need to be dissolved or suspended in a fluid before testing in accordance with the principles of the method described below can be carried out, but a modified testing method in accordance with the invention, may be carried out on a solid or even gaseous sample.

More particularly, the method described below by way of example, is for providing an indication as to the number of cells in a milk sample in order to determine whether the animal from which the milk was obtained, is suffering from any serious infection, most particularly, mastitis.

Figure 1:
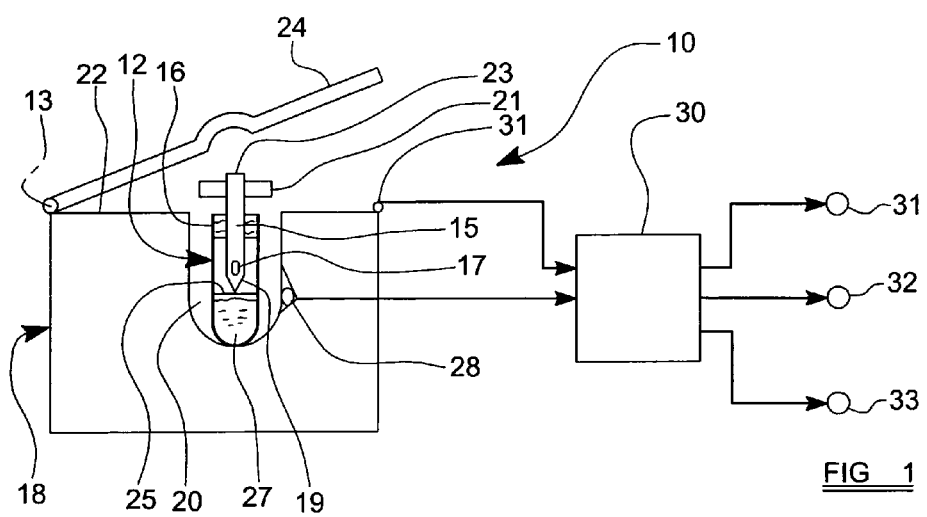
FIG. 1 is an illustrative view of an apparatus for use in the method of the invention, including a testing container received in a light detecting device.

The apparatus 10 includes a testing container 12 which in this example is a test tube, but in any event the testing container 12 is transparent or at least has a window of transparency for the purpose hereinafter described. In FIG. 1, the testing container is shown containing a dipstick 15. The dipstick 15, during testing, is mounted by a fluid tight closure 16 so as to depend within the container 12. However, the dipstick 15, together with the closure 16 in this example, may be provided separately from the testing container 12 e.g. in a protective sheath or the like, from which the dipstick 15 may be removed to enable the dipstick 15 to be dipped into a fluid to be tested to attach a sample of the fluid to the dipstick 15. Preferably, immediately after collecting the sample, the dipstick 15 is placed or replaced in the testing container 16 in the condition shown in FIG. 1, to prevent the sample becoming contaminated.

Thus the dipstick 15 includes an attachment part 17 provided by an absorbent material, such as a foamed plastic. By ensuring that the attachment part 17 size is uniform across a batch of dipsticks 15, test results from a plurality of dipsticks 15 should be comparable, as the absorbent material in each of the dipsticks 15 of the batch of dipsticks 15 will absorb substantially the same amount of the fluid, and thus the fluid sample sizes will be substantially the same.

A reagent containing an enzyme, is pre-absorbed and dried, on the attachment part 17. For one example, a mixture of Luciferin and the enzyme Luciferase may be pre-absorbed by the absorbent material.

The apparatus 10 further includes a light detecting device 18, which is configured to count light scintillations occurring in the testing container 16 as a result of a reaction described below. Hence the need for the testing container 16 to be transparent or have a window of transparency at least.

The light detecting device 18 in this example includes a recess 20 to receive the testing container 16. When the testing container 12 is received in the recess 20, it can be seen that an upper end 23 of the dipstick 15 stands proud of the recess 20, extending above an uppermost surface 22 of a part of the device 18 around the recess 20.

The light detecting device 18 includes a lid 24 which is hinged at 13 to the part of the device 18 having the recess 20. When the lid 24 is closed, the lid 24 will engage the upper end 23 of the dipstick 15 and if lid 24 movement is continued, the dipstick 15 will be moved down relative to the closure 16, in the testing container 12. When the lid 24 is closed, the recess 20 is closed and light tight.

Within the testing container 12 there is a membrane 25 made of a suitable readily frangible or at least puncturable, or breakable, or otherwise rupturable, material such as metalised Mylar, polyethylene or polypropylene, or another readily frangible material. The membrane 25 serves to isolate within the testing container 12 out of contact with the attachment part 17 of the dipstick 15, another reagent namely an extractant 27 being a Lysate in this example. However when the lid 24 of the light detecting device 18 is closed and the dipstick 15 is moved down, a pointed lowermost end 19 of the dipstick 15 will be forced through the membrane 25 and the Lysate extractant 27 will contact the attachment part 17, and more particularly, the sample attached.

The testing method will now be explained.

First a milk sample is collected by dipping the dipstick 15 into the milk. This is carried out with the testing container 12 out of the light detecting device 18, e.g. carried in a readily portable holder with other testing containers 16 for collecting other samples When the dipstick 15 is dipped into the milk, a predetermined volume of the milk will attach to the attachment part 17, to provide the sample to be tested. Immediately afterwards, the dipstick 15 and closure 16 are placed or replaced in the testing container 12.

The Luciferin in the presence of the enzyme on the attachment part 17 will begin to react with any free ATP (which term includes any other material which may be present in the sample which reacts with the enzyme to produce light emissions) which may be in the milk sample, immediately that the sample contacts the reagent. The reaction is such that the reaction will produce light scintillations.

Subsequently, typically after a short time the dairyman will, for example, test the sample at a testing station where the light detecting device 18 may be located, by placing the testing container 12 into the recess 20 of the device 18 and closing the lid 24 to move the dipstick 15 in the testing container 12 downwards as seen in FIG. 1, so that the pointed end 19 ruptures the membrane 25, and the sample on the attachment part 17 of the dipstick 15 is brought into contact with the extractant 27.

Substantially simultaneously with contacting the sample with the extractant 27, the light detecting device 18 will begin to detect light scintillations. In FIG. 1, for illustrative purposes only, a light sensor 28 is shown which provides an input to a controller 30, when the sensor 28 senses that the lid 24 has been closed and that a measurement period has begun. The light sensor may for example be a photo-multiplier tube.

As will be described below, during or after a measurement period, the controller 30 will either produce a signal e.g. to illuminate a first light emitting device 31 which will indicate that the test is void because the light scintillations detected indicate that too great a level of ATP to be present for the test to be meaningful (often as a result of sample contamination), or the controller 30 will produce a signal to illuminate a second light emitting device 32 which indicates that the number of cells present within the sample, which have been ruptured to release cell-bound ATP have been determined to be below a threshold limit, which indicates that the animal from which the milk sample was taken is unlikely to have any serious infection, or the controller 30 will produce a signal to illuminate a third light emitting device 33 which indicates that the level of bacteria and/or number of somatic cells present within the sample, which have been ruptured to release cell-bound ATP have been determined to be above a threshold limit, which indicates that the animal from which the milk sample was taken is likely to have a serious infection.

Figure 2:
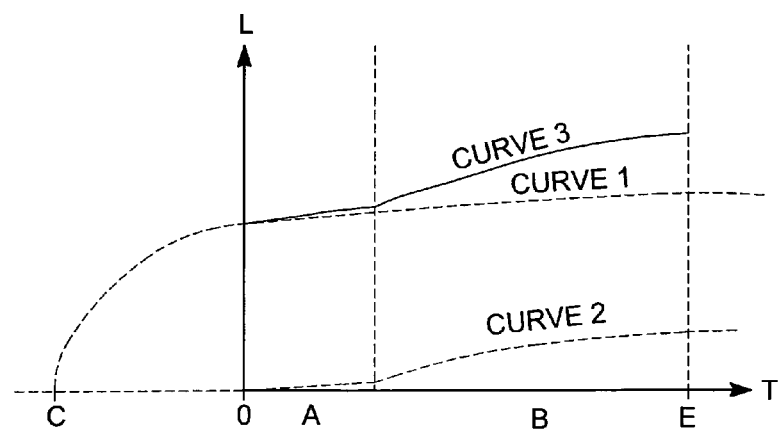
FIG. 2 is an illustrative graphical representation to used below to explain the method of the invention.

Referring to FIG. 2, at the commencement of the measurement period, in an initial period, which may be only a few seconds, such as two seconds, it is illustrated that the light scintillations detected by the light sensor 28, will not largely be due to the reaction of the released ATP and the Luciferin and enzyme reagent. Since sample collection, indicated at time C on the x-axis of the graph, the free ATP will be reacting with the reagent and producing light scintillations at the level shown along the y-axis. At commencement of the measurement period, indicated at O, the contribution to light scintillations due to cell-bound ATP being released from any cells present due to the action of the extractant, will be minor, and so during the initial period of measurement indicated at A, the contribution to light scintillations sensed due to released cell-bound ATP reacting with the reagent can effectively be ignored.

If during the initial measurement period A, a very high level of light scintillations were detected, this would indicate that the sample contains very high levels of free ATP. This could be due to a serious problem with the animal from where the milk is collected, or may be due to the sample being contaminated e.g. with animal excrement. If the sensor 28 senses light scintillations above a maximum level during the initial measurement period, the controller 30 will illuminate light emitting device 31, or provide an alternative warning signal. If the level of free ATP indicated is so high that this would make subsequent testing of the sample inaccurate or even impossible, the test may be curtailed at that point, but the test may continue if a meaningful indication of the level of cell-bound ATP being released from the sample by the action of the extractant can still be derived.

In normal circumstances though, when light scintillation levels above the maximum level are not detected in the initial measurement period, or at least are not so high that the test needs to be curtailed, by determining the light scintillation level at least once in the initial period of measurement A, the changing level of light emissions due to the ATP released from the cells reacting with the reagent over the remainder of the measurement period can be determined. In FIG. 2, for simplicity, the level L of light scintillations due to the reaction of the free ATP with the reagent, is shown to have reached a substantially steady state since sample collection time O, and thus the contribution to light scintillations as the free ATP reacts with the reagent, may be substantially steady over the initial measurement period A. Practically though, the situation will be more complex than this, but in most cases though, enough data can be gleaned by determining the level of light scintillations at least one point in the initial measurement period A, for a determination of the rate of change of the light scintillation level due to the released ATP reacting with the reagent over the remainder of the measurement period B, to be made, e.g. as shown by curve 3 in the graph.

In this example the contribution to light scintillations due to cell-bound ATP being released and reacting with the reagent, as indicated by curve 2, is shown increasing and becoming more significant compared to the light scintillation level due to the free ATP reacting with the reagent, but in another example, where little free ATP is present, the various curves may look very different.

Curve 3 shown on the graph, is indicative of the total level of light scintillations detected. By determining the instantaneous light level at intervals during the further measurement period B, and performing a statistical analysis using the determination of light scintillation level in the initial measurement period A, a best fit for curve 3 can be determined to indicate the changing level of light scintillations due to the released ATP reacting with the reagent.

In the example, over the measurement period A, B, at least several instantaneous readings are taken. The curves curve 1 and curve 3 are the interpolated to give the "best fits" from the data available, and rate of change of light emissions can be used to determine the level of bacteria and/or the number of somatic cells present in the sample.

One or other of the second and third light emitting devices 32, 33 will be illuminated by respective signals, from the controller 30 to indicate either that the sample has passed the test (light emitting device 32 illuminated) or has failed the test (light emitting device 33 illuminated). In this latter case, the test will have indicated that the number of somatic or other cells present in the sample is above a threshold such that there is a strong likelihood that the animal from which the milk sample was taken has a serious infection. From then on, more formal testing and perhaps examination of the animal by a veterinary surgeon would be required.

Various modifications are possible without departing from the scope of the invention.

It will be appreciated that the construction of the light detecting device 18 in FIG. 1 is purely illustrative and the invention may utilise a light detecting device of a very different construction. Moreover the configuration of the testing container 12 is purely exemplary and may be modified. For example, in the example shown, the dipstick 15 within the testing container 12 includes a region 21 where it is intended an indicator, such as a label, may be provided, so that during sample taking, the identity of the animal or other specific information about the identity of the sample, can be recorded. In another example, this may be omitted, or some other mechanism for recording information relating to the origin of the sample may be provided.

In another testing application, for example in an application where the organic sample to be tested is not a fluid into which a dipstick may be dipped, instead of a dipstick, an attachment part of a swab or the like may be used to collect a predetermined volume of the sample. Thus the organic sample tested may be collected from a surface. As indicated above, the sample to be tested may be a solid and may require to be dissolved or otherwise provided in a fluid form, for testing. Thus the sample need not be collected on a dipstick, and may not be brought into contact with the extractant in a testing container which includes the membrane.

For example, a membrane need not be provided in the testing container 12, but when the dipstick is placed in the testing container 12, this may bring the sample collected into direct contact with the extractant.

In another method, the dipstick 15, after sample collection, with or without the sample, may be placed in a storage container. The dipstick 15 may be transferred to a testing container 12 which contains extractant but need not contain any membrane as in the example described above, immediately prior to placing the testing container 12 in the light detecting device 18. Preferably, but not essentially, the dipstick 15 may again be moved down in the testing container 12 by closing the lid 24, to contact the sample/reagent and extractant. Alternatively on transferring the dipstick 15 to the testing container 12, the sample/reagent may be brought into contact with the extractant.

To avoid the need to have a specific method step to contact the sample with the reagent, the reagent is provided in or on the dipstick, swab or other sample collecting device, and even though any free ATP present may immediately begin reacting with the reagent, as will be appreciated from the explanation above, this need not be detrimental to the testing method of the present invention.

It will be appreciated though, that the reagent may become spent after a time from when the sample was taken, particularly if there is much free ATP present in the sample. Preferably therefore testing is commenced within a specified time window from when the sample was taken, e.g. within 30 minutes or so.

In another example, instead of using a reagent being a mixture of Luciferin and the enzyme Luciferase pre-absorbed by the absorbent material of the dipstick 15 or other sample collecting device, an other suitable reagent could be used. Also, instead of the extractant 27 in the testing container 12 being a Lysate, another suitable extractant, to rupture cells to release cell-bound ATP therein, may be utilised.

The threshold level at which the controller 30 provides the signal to illuminate the third light emitting device 33 may be set by calibration of the apparatus 10. Instead of light emitting devices such as indicated at 31-33, some other device which is able to provide an indication at least, that in a sample being tested, the level of bacteria and/or number of somatic cells present is determined to be above a threshold, may be signalled, such as an audible device, or perhaps merely a data print out or computer screen indication.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A method of testing an organic sample to provide an indication of a level of bacteria and/or somatic cells present in the sample represented by light emissions, the method comprising the steps of:
   a) collecting the sample,
   b) contacting the sample with a reagent, which reacts with ATP present in the sample to produce light emissions,
   c) subsequent to step b), contacting the sample with an extractant, which ruptures cells present in the sample to release cell-bound ATP, d) immediately after step c), in an initial measurement period, measuring a first level of light emissions, as the cell-bound ATP begins to be released, to minimize light emissions due to the cell-bound ATP being released and reacting with the reagent, e) subsequent to step d), in a subsequent measurement period, measuring a subsequent level of light emissions, as the cell-bound ATP is released and reacts with the reagent to measure light emissions due to the cell-bound ATP being released and reacting with the reagent, and f) determining, from the levels of light emissions measured in steps d) and e), whether the levels of light emissions are above a pre-set threshold.

2. A method according to claim 1, wherein the organic sample is fluid collected on a dipstick having an attachment part to which a predetermined volume of the sample may attach as the dipstick is dipped into the sample that is to be collected.

3. A method according to claim 2, wherein the attachment part is impregnated with the reagent.

4. A method according to claim 1, wherein the extractant is maintained out of contact with the sample and reagent until the beginning of the initial measurement period.

5. A method according to claim 4, wherein the extractant is maintained out of contact with the sample and reagent by a membrane within a testing container, and the sample is contacted with the extractant by moving the dipstick in the testing container so as to rupture the membrane.

6. A method according to claim 5, wherein the dipstick movement is achieved with the testing container positioned in a chamber of a light detecting device, by moving a part of the light detecting device to engage the dipstick, and to move the dipstick into the extractant.

7. A method according to claim 4, wherein the dipstick is moved in a testing container to contact the extractant and the sample and the reagent.

8. A method according to claim 1, further comprising the step of generating a signal when levels of light emissions are above a preset threshold, wherein the signal provides a warning.

9. A method according to claim 1, wherein the subsequent level of light emissions are measured at intervals over the subsequent measurement period.

10. A method of testing an organic sample to provide an indication of the level of bacteria and/or somatic cells present in the sample represented by light emission, the method comprising the steps of:

a) collecting the sample, b) contacting the sample with a reagent, which reacts with ATP present in the sample to produce light emissions, c) subsequent to step b), contacting the sample with an extractant, which ruptures cells present in the sample so as to release cell-bound ATP, d) immediately after step c), in an initial measurement period, measuring a first level of light emissions, using a light detecting device, just prior to the cell-bound ATP being released, so that a contribution of light emissions due to the cell-bound ATP being released and reacting with the reagent is minimized, e) subsequent to step d), in a subsequent measurement period, without adding an additional substance, measuring subsequent levels of light emissions, using the light detecting device, as the cell-bound ATP is released and reacts with the reagent so that an increase in the subsequent levels of light emissions over the first level of light emissions are due to the cell-bound ATP being released and reacting with the reagent, and f) determining, from the levels of light emissions measured in steps d) and e), over the measurement periods, whether the levels of light emissions are above a pre-set threshold.

11. A method according to claim 10, wherein the organic sample is fluid collected on a dipstick having an attachment part to which a predetermined volume of the sample may attach as the dipstick is dipped into the sample that is to be collected.

12. A method according to claim 11, wherein the attachment part is impregnated with the reagent.

13. A method according to claim 10, wherein the extractant is maintained out of contact with the sample and reagent until the beginning of the initial measurement period.

14. A method according to claim 13, wherein the extractant is maintained out of contact with the sample and reagent by a membrane within a testing container, and the sample is contacted with the extractant by moving the dipstick in the testing container so as to rupture the membrane.

15. A method according to claim 14, wherein the dipstick movement is achieved with the testing container positioned in a chamber of a light detecting device, by moving a part of the light detecting device to engage the dipstick, and to move the dipstick into the extractant.

16. A method according to claim 13, wherein the dipstick is moved in a testing container to contact the extractant and the sample and the reagent.

17. A method according to claim 10, further comprising the step of generating a signal when levels of light emissions are above a preset threshold, wherein the signal provides a warning.

18. A method according to claim 10, wherein the subsequent levels of light emissions are measured at intervals over the subsequent measurement period.

19. A method of testing an organic sample to provide an indication of the level of bacteria and/or somatic cells present in the sample represented by light emissions, the method comprising the steps of:

a) collecting the sample, b) contacting the sample with a reagent, which reacts with ATP present in the sample to produce light emissions, c) subsequent to step b), contacting the sample with an extractant, which ruptures cells present in the sample so as to release cell-bound ATP, d) immediately after step c), in an initial measurement period, measuring a first level of light emissions, using a light detecting device, as the cell-bound ATP begins to be released, so that a contribution of light emissions due to the cell-bound ATP being released and reacting with the reagent is minimized, e) immediately after step d), in a subsequent measurement period, without adding an additional substance, measuring subsequent levels of light emissions, using the light detecting device, as the cell-bound ATP is released and reacts with the reagent so that any increase in the subsequent levels of light emissions over the first level of light emissions is due to the cell-bound ATP being released and reacting with the reagent, f) determining, from the levels of light emissions measured and relative changes in light emissions produced in steps d) and e), over the measurement periods, whether the levels of light emissions are above pre-set thresholds; and if the levels of light emissions are above pre-set thresholds, individual signals are generated.

20. A method according to claim 19, wherein the subsequent levels of light emissions are measured at intervals over the subsequent measurement period.

* * * * *